United States Patent
Miller et al.

(10) Patent No.: US 7,466,120 B2
(45) Date of Patent: Dec. 16, 2008

(54) COMMUNICATING WITH AN IMPLANTED WIRELESS SENSOR

(75) Inventors: Donald J. Miller, Roswell, GA (US); Michael G. Ellis, Alpharetta, GA (US); Mark G. Allen, Atlanta, GA (US)

(73) Assignee: CardioMEMS, Inc., Atlanta, GA (US)

( * ) Notice: Subject to any disclaimer, the term of this patent is extended or adjusted under 35 U.S.C. 154(b) by 0 days.

(21) Appl. No.: 11/717,967

(22) Filed: Mar. 14, 2007

(65) Prior Publication Data

US 2007/0247138 A1 Oct. 25, 2007

Related U.S. Application Data

(63) Continuation-in-part of application No. 11/276,571, filed on Mar. 6, 2006, which is a continuation-in-part of application No. 11/105,294, filed on Apr. 13, 2005, now Pat. No. 7,245,117.

(60) Provisional application No. 60/782,313, filed on Mar. 14, 2006, provisional application No. 60/623,959, filed on Nov. 1, 2004.

(51) Int. Cl.
G01R 23/12 (2006.01)
G01R 35/00 (2006.01)

(52) U.S. Cl. .................. 324/76.51; 324/76.52; 324/601

(58) Field of Classification Search .............. 324/76.51, 324/76.52, 601
See application file for complete search history.

(56) References Cited

U.S. PATENT DOCUMENTS

| | | | |
|---|---|---|---|
| 2,769,863 A | 6/1957 | Graybill et al. | |
| 3,867,950 A | 2/1975 | Fischell | |
| 3,882,424 A | 5/1975 | Debois et al. | |
| 3,913,028 A | 10/1975 | Bosselaers | |
| 3,942,382 A | 3/1976 | Hok | |
| 3,958,558 A | 5/1976 | Dunphy et al. | |
| 4,026,276 A | 5/1977 | Chubbuck | |
| 4,114,606 A | 9/1978 | Seylar | |

(Continued)

FOREIGN PATENT DOCUMENTS

CA 1158061 6/1983

(Continued)

OTHER PUBLICATIONS

U.S. Appl. No. 11/276,571, filed Jul. 23, 2007, Allen et al.

(Continued)

*Primary Examiner*—Timothy J Dole
(74) *Attorney, Agent, or Firm*—Kilpatrick Stockton LLP (57) ABSTRACT

Aspects of the present invention determine the resonant frequency of a sensor by obtaining sensor signals in response to three energizing signals, measuring the phase of each sensor signal, and using a group phase delay to determine the resonant frequency. The phase difference between the first and second signal is determined as a first group phase delay. The phase difference between the second and third signal is determined as a second group phase delay. The first group phase delay and second group phase delay are compared. Based on the comparison, the system may lock on the resonant frequency of the sensor or adjust a subsequent set of three energizing signals.

23 Claims, 10 Drawing Sheets

U.S. PATENT DOCUMENTS

| | | | |
|---|---|---|---|
| 4,127,110 A | 11/1978 | Bullara | |
| 4,152,669 A | 5/1979 | Igarashi | |
| 4,206,762 A | 6/1980 | Cosman | |
| 4,207,903 A | 6/1980 | O'Neil | |
| 4,237,900 A | 12/1980 | Schulman et al. | |
| 4,354,506 A | 10/1982 | Sakaguchi et al. | |
| 4,378,809 A | 4/1983 | Cosman | |
| 4,485,813 A | 12/1984 | Anderson et al. | |
| 4,494,950 A | 1/1985 | Fischell | |
| 4,521,684 A | 6/1985 | Gilby et al. | |
| 4,531,526 A | 7/1985 | Genest | |
| 4,593,703 A | 6/1986 | Cosman et al. | |
| 4,596,563 A | 6/1986 | Pande | |
| 4,713,540 A | 12/1987 | Gilby et al. | |
| 4,718,425 A | 1/1988 | Tanaka et al. | |
| 4,720,687 A | 1/1988 | Ostoich et al. | |
| 4,796,641 A | 1/1989 | Mills et al. | |
| 4,815,472 A | 3/1989 | Wise et al. | |
| 4,846,191 A | 7/1989 | Brockway et al. | |
| 4,890,623 A | 1/1990 | Cook et al. | |
| 4,899,752 A | 2/1990 | Cohen | |
| 4,913,147 A | 4/1990 | Fahlstrom et al. | |
| 4,934,369 A | 6/1990 | Maxwell | |
| 4,987,897 A | 1/1991 | Funke | |
| 5,113,868 A | 5/1992 | Wise et al. | |
| 5,115,128 A | 5/1992 | Cook | |
| 5,129,394 A | 7/1992 | Mehra | |
| 5,148,123 A | 9/1992 | Ries | |
| 5,165,289 A | 11/1992 | Tilmans | |
| 5,181,423 A | 1/1993 | Philipps et al. | |
| 5,192,314 A | 3/1993 | Daskalakis | |
| 5,207,103 A | 5/1993 | Wise et al. | |
| 5,265,606 A | 11/1993 | Kujawski | |
| 5,353,800 A | 10/1994 | Pohndorf et al. | |
| 5,373,852 A | 12/1994 | Harrison et al. | |
| 5,411,551 A | 5/1995 | Winston et al. | |
| 5,431,171 A | 7/1995 | Harrison et al. | |
| 5,440,300 A | 8/1995 | Spillman, Jr. | |
| 5,487,760 A | 1/1996 | Villafana | |
| 5,497,099 A | 3/1996 | Walton | |
| 5,515,041 A | 5/1996 | Spillman, Jr. | |
| 5,535,752 A | 7/1996 | Halperin et al. | |
| 5,538,005 A | 7/1996 | Harrison et al. | |
| 5,551,427 A | 9/1996 | Altman | |
| 5,566,676 A | 10/1996 | Rosenfeldt et al. | |
| 5,593,430 A | 1/1997 | Renger | |
| 5,594,389 A | 1/1997 | Kiyanagi et al. | |
| 5,600,245 A | 2/1997 | Yamamoto et al. | |
| 5,625,341 A * | 4/1997 | Giles et al. | 340/10.34 |
| 5,626,630 A | 5/1997 | Markowitz et al. | |
| 5,686,841 A | 11/1997 | Stolarczyk et al. | |
| 5,695,155 A | 12/1997 | Macdonald et al. | |
| 5,702,427 A | 12/1997 | Ecker et al. | |
| 5,703,576 A | 12/1997 | Spillman, Jr. et al. | |
| 5,713,917 A | 2/1998 | Leonhardt et al. | |
| 5,722,414 A | 3/1998 | Archibald et al. | |
| 5,723,791 A | 3/1998 | Koch et al. | |
| 5,743,267 A | 4/1998 | Nikolic et al. | |
| 5,796,827 A | 8/1998 | Coppersmith et al. | |
| 5,807,265 A | 9/1998 | Itoigawa et al. | |
| 5,836,886 A | 11/1998 | Itoigawa et al. | |
| 5,860,938 A | 1/1999 | Lafontaine et al. | |
| 5,896,113 A | 4/1999 | O'Neill, Jr. | |
| 5,899,927 A | 5/1999 | Ecker et al. | |
| 5,935,084 A | 8/1999 | Southworth | |
| 5,942,991 A | 8/1999 | Gaudreau et al. | |
| 5,967,986 A | 10/1999 | Cimochowski et al. | |
| 6,015,386 A | 1/2000 | Kensey et al. | |
| 6,015,387 A | 1/2000 | Schwartz et al. | |
| 6,019,729 A | 2/2000 | Itoigawa et al. | |
| 6,024,704 A | 2/2000 | Meador et al. | |
| 6,025,725 A | 2/2000 | Gershenfeld et al. | |
| 6,030,413 A | 2/2000 | Lazarus | |
| 6,033,366 A | 3/2000 | Brockway et al. | |
| 6,053,873 A | 4/2000 | Govari et al. | |
| 6,076,016 A | 6/2000 | Feierbach | |
| 6,111,520 A * | 8/2000 | Allen et al. | 324/655 |
| 6,113,553 A | 9/2000 | Chubbuck | |
| 6,134,461 A | 10/2000 | Say et al. | |
| 6,140,740 A | 10/2000 | Porat et al. | |
| 6,159,156 A | 12/2000 | Van Bockel | |
| 6,165,135 A | 12/2000 | Neff | |
| 6,198,965 B1 | 3/2001 | Penner et al. | |
| 6,201,980 B1 | 3/2001 | Darrow et al. | |
| 6,206,835 B1 | 3/2001 | Spillman, Jr. et al. | |
| 6,237,398 B1 | 5/2001 | Porat et al. | |
| 6,239,724 B1 | 5/2001 | Doron et al. | |
| 6,259,328 B1 * | 7/2001 | Wesolowski | 331/14 |
| 6,277,078 B1 | 8/2001 | Porat et al. | |
| 6,278,379 B1 * | 8/2001 | Allen et al. | 324/655 |
| 6,287,253 B1 | 9/2001 | Ortega et al. | |
| 6,331,792 B1 | 12/2001 | Tonietto | |
| 6,373,264 B1 | 4/2002 | Matsumoto et al. | |
| 6,409,674 B1 | 6/2002 | Brockway et al. | |
| 6,411,130 B1 | 6/2002 | Gater | |
| 6,442,413 B1 | 8/2002 | Silver | |
| 6,454,720 B1 | 9/2002 | Clerc et al. | |
| 6,577,893 B1 | 6/2003 | Besson | |
| 6,645,143 B2 | 11/2003 | VanTassel et al. | |
| 6,667,725 B1 | 12/2003 | Simons et al. | |
| 9,743,183 | 6/2004 | Thornton | |
| 6,765,493 B2 | 7/2004 | Lonsdale et al. | |
| 6,855,115 B2 * | 2/2005 | Fonseca et al. | 600/488 |
| 6,923,769 B2 | 8/2005 | Nishii et al. | |
| 6,926,670 B2 | 8/2005 | Rich et al. | |
| 7,076,215 B1 | 7/2006 | Moliere | |
| 7,233,182 B1 | 6/2007 | Savoj | |
| 7,245,117 B1 * | 7/2007 | Joy et al. | 324/76.52 |
| 2002/0151816 A1 | 10/2002 | Rich et al. | |
| 2002/0188207 A1 | 12/2002 | Richter | |
| 2003/0031587 A1 | 2/2003 | Hu et al. | |
| 2003/0136417 A1 * | 7/2003 | Fonseca et al. | 128/899 |
| 2003/0139677 A1 | 7/2003 | Fonseca et al. | |
| 2003/0151400 A1 * | 8/2003 | Petrovich et al. | 324/76.52 |
| 2003/0185330 A1 | 10/2003 | Hessel et al. | |
| 2004/0122494 A1 | 6/2004 | Eggers et al. | |
| 2005/0075697 A1 | 4/2005 | Olson et al. | |
| 2005/0085703 A1 | 4/2005 | Behm | |
| 2005/0154321 A1 | 7/2005 | Wolinsky et al. | |
| 2006/0196277 A1 * | 9/2006 | Allen et al. | 73/861.12 |
| 2007/0096715 A1 * | 5/2007 | Joy et al. | 324/76.53 |
| 2007/0100215 A1 | 5/2007 | Powers et al. | |
| 2007/0210786 A1 | 9/2007 | Allen et al | |

FOREIGN PATENT DOCUMENTS

| | | |
|---|---|---|
| DE | 19644858.5 | 10/1996 |
| EP | 0337035 | 11/1993 |
| EP | 0646365 | 4/1995 |
| WO | WO 83/03348 | 10/1983 |
| WO | WO 90/06723 | 6/1990 |
| WO | WO 95/33517 | 12/1995 |
| WO | WO 97/09926 | 3/1997 |
| WO | WO 1997/11641 A | 4/1997 |
| WO | WO 97/32518 | 9/1997 |
| WO | WO 97/32519 | 9/1997 |
| WO | WO 97/33513 | 9/1997 |
| WO | WO 99/34731 | 7/1999 |
| WO | WO 00/16686 | 3/2000 |
| WO | WO 01/00089 | 1/2001 |
| WO | WO 01/87137 | 11/2001 |
| WO | WO 01/97908 A2 | 12/2001 |
| WO | WO 2003/032009 | 4/2003 |
| WO | WO 03/061504 A1 | 7/2003 |

| | | |
|---|---|---|
| WO | WO 98/47727 A | 10/2003 |
| WO | WO 2005/027998 | 3/2005 |
| WO | WO 2006/049796 | 5/2006 |
| WO | WO 2006/096582 | 9/2006 |
| WO | WO 2007/030489 | 3/2007 |
| WO | WO 2007/106490 | 9/2007 |

OTHER PUBLICATIONS

A. Deheenis, K.D. Wise; "A Passive-Telemetry-Based Pressure Sensing System": NSF Engineering Research Center For Wireless Integrated Microsystems; Department of Electrical Engineering and Computer Science; The University of Michigan, Ann Arbor, MI 48109-2122 US, no date.

S.R. Vallabhane, J. Brennan, G. Gilling-Smith, D. Gould, T. How, R. McWilliams, P.L. Harris; "Aortic Side Branch perfusion Alone Does Not Account For High Intra-Sac Pressure After Endovascular Repair (EVAR) In the Absence of Graft-Related Endoleak"; Royal Liverpool University Hospital, Liverpool, UK, no date.

M. Gawenda, J. Heckenkamp, M. Zaehringer, J. Brunkwall; "Intra-Aneurysm Sac Pressure-The Holy Gail of Endoluminal Grafting of AAA"; Eur J Vasc Endovasc Surg, vol. 24, Aug. 2002, pp. 139-145.

GWH Schurink, NJM Arts, J Wild, J.M Van Baalen, Tam Chutner, LJ Schultze Kool, JH Van Bockel; "Endoleakage After Stent-Graft Treatment of Abdominal Aneurysm: Implications On Pressure and Imaging-An In Vitro Study"; Journal of Vascular Surgery, vol. 28, No. 2, pp. 234-241, no date.

B. Sonesson, N. Dias, M. Malina, P. Olofsson, D. Griffin, B. Lindblad, K. Ivancev; "Intra-Aneurysm Pressure Measurements In Successfully Excluded Abdominal Aortic Aneurysm After Endovascular Repair"; Journal of Vascular Surgery, vol. 37, No. 4, Apr. 2003, pp. 733-738.

C.S. Skillern, S.L. Stevens, K.T. Piercy, R.L. Donnell, M.B. Freeman, M.H. Goldman; "Endotension In An Experimental Aneurysm Model"; Journal of Vascular Surgery, vol. 36, No. 4, Oct. 2002, pp. 814-817.

G.D. Treharne, I.M. Loftus, M.M. Thompson, N. Leonard, J. Smith, G. Fishwick, PRF Bell; "Quality Control During Endovascular Aneurysm Repair: Monitoring Aneurysmal Sac Pressure And Superficial Femoral Artery Flow Velocity"; J. Endovasc Surg, 1999, 6, pp. 239-245.

M.L. Manwaring, V.D. Malbasa, K.L. Manwaring: "Remote Monitoring of Intercranial Pressure"; Institute of Concology; Annals of the Academy of Studencia Apr. 2001; pp. 77-80.

GWH Schurink, NJM Arts, J.M. Van Baalen, L.J. Schultze Kool, JH Van Bockel; "Experimental Study of the Influence of Endoleakage Size on Pressure in the Aneurysm Sac and the Consequences of Thrombosis"; Bristish Journal of Surgery 2002, 87, pp. 71-78.

K. Ouriel; "Role of Intrasac Pressure Measurements After EVAR: Can They Be Followed Noninvasively?"; Combined Session: Vascular Surgery and Interventional Radiology; VII 4.1, no date.

R.A. Baum, J.P. Carpenter, C. Cope, M.A. Golden, O.C. Velazquez, D.G. Neschis, M.E. Mitchell, C.F. Barker, R.M. Fairman; "Aneurysm Sac Pressure measurements After Endovascular Repair of Abdominal Aortic Aneurysms"; Journal of Vascular Surgery, vol. 33, No. 1, Jan. 2001, pp. 32-41.

P.L. Harris, S. Dimitri; "Predicting failure of endovascular Aneurysm repair"; Eur J Vas Endovasc Surg, vol. 17, Jan. 1999; pp. 1-2.

G. Akingba, A. Cheng, A. Shum, P. Yang; "An Implantable Pressure Sensor for Aneurysmal Disease", no date.

K.F. Adams, Jr.; "Guiding Heart Failure Care by Invasive Hemodynamic Measurements: Possible Or Useful?"; Journal of cardiac failure, vol. 8, No. 2, Apr. 2002, pp. 71-73.

A. Magalski, P. Adamson, F. Gadler, M. Boehm, D. Steinhaus, D. Reynolds, K. Vlach, C. Linde, B. Cremers, B. Sparks, T. Bennet; "Continuous Ambulatory Right Heart Presure Measurements with an Implantable Hemodynamic Monitor: A Multicenter, 12-Month Follow-Up Study of Patients with Chronic Heart Failure"; Journal of Cardiac failure, vol. 8, Apr. 2002, pp. 63-70.

R. Shabetai; "Monitoring Heart Failure Hemodynamics with an Implanted Device: Its Potential to Improve Outcome"; Journal of the American College of Cardiology; vol. 41, No. 4, Feb. 19, 2003; pp. 572-573.

J.C. Parodi, R. Berguer, L.M. Ferreira, R. Lamura, M.L. Schererhorn; "Intra-eneurysmal Pressure After Incomplete Endovascular Exclusion"; Journal of Vascular Surgery, vol. 24, No. 5, Nov. 2001, pp. 909-914.

M. Gawenda, J. Heckenkamp, S. Winter, G. Jaschke, J. Brunkwall; Pressure is Transmitted Through PTFE and Dacron Grafts Leading the Aneurysm Sac Pressure Endoluminal Grafting of AAA—An In Vitro Study; Vascular Centre, university of Cologne, Germany, no date.

T. Akin, B. Ziaie, K. Najafi; "RF Telemetry Powering and Controlling of Hermetically Sealed Integrated Sensors and Actuators", Center for Integrated Sensors and Circuits; Department of Electrical Engineering and Computer Science; University of Michigan; Ann Arbor, Michigan 48109-2122; pp. 145-148, no date.

H.E. Haynes, A.L. Witchey; "Medical electronics: The Pill That Talks"; DEP, Camden, N.J, no date.

A. Dehennis, K.D. Wise; "A Double-Sided Single-Chip Wireless Pressure Sensor": Engineering Research Center For Wireless Integrated Microsystems; Department of Electrical Engineering and Computer Science; The University of Michigan, Ann Arbor, MI 48109-2122 US, no date.

J. Zhe, R.R. Farmer, V. Modi; "A MEMS Device For Measurement of Skin Friction with Capacitive Sensing"; Department of Mechanical Engineering, Columbia university, NY 10027; Microelectronics research Center, New Jersey Institute of Technology, Newark, NJ 07102, no date.

T. Chuter, K. Ivancev, M. Malina, T. Resch, J. Brunkwall, B. Lindblad, B. Risberg; "Endovascular and Surgical techniques"; Eur J. Vasc Endovasc Surg vol. 13, Jan. 1997, pp. 85-87.

J.T. Farrar, C. Berkley, V.K. Zworykin; "Telemetering of Intraenteric pressure In man By An Externally Energized Wireless Capsule"; Science, New Series, vol. 131, Issue 3416 (Jun. 17, 1960), 1814.

Harpster, "A Passive Wireless Integrated Humidity Sensor", Micro Electro Mechanical Systems, 2001, pp. 553-557.

Fonseca, "High Temperature Characterization of Ceramic Pressure Sensors", vol. 1, 2001, pp. 486-489.

Allen, "Micromachined Endovascularly Implantable Wireless Aneurysm Pressure Sensors", No. 13, 2005, pp. 275-278.

Seifert, "Wirelessly Interrogable Acoustic Sensors", No. 2, 1999, pp. 1013-1018.

* cited by examiner

COMMUNICATING WITH AN IMPLANTED WIRELESS SENSOR

RELATED APPLICATIONS

This application is a continuation-in-part of U.S. application Ser. No. 11/276,571 entitled "Communicating with an Implanted Wireless Sensor" filed Mar. 6, 2006, which is a continuation-in-part of U.S. application Ser. No. 11/105,294 entitled "Communicating with an Implanted Wireless Sensor" filed Apr. 13, 2005 now U.S. Pat. No. 7,245,117, which claims priority to U.S. Provisional Application No. 60/623,959 entitled "Communicating with an Implanted Wireless Sensor" filed Nov. 1, 2004, all of which are incorporated herein by reference. This application also claims priority to U.S. Provisional Application No. 60/782,313 filed Mar. 14, 2006, which is also incorporated herein by reference.

TECHNICAL FIELD

The present invention is directed in general to communicating with a wireless sensor, and in particular to communicating with a wireless sensor implanted within the body to measure a physical condition.

BACKGROUND

Wireless sensors can be implanted within the body and used to monitor physical conditions, such as pressure or temperature. For example, U.S. Pat. No. 6,111,520, U.S. Pat. No. 6,855,115 and U.S. Publication No. 2003/0136417, each of which is incorporated herein by reference, all describe wireless sensors that can be implanted within the body. These sensors can be used to monitor physical conditions within the heart or an abdominal aneurysm. An abdominal aortic aneurysm (AAA) is a dilatation and weakening of the abdominal aorta that can lead to aortic rupture and sudden death. In the case of a repaired abdominal aneurysm, a sensor can be used to monitor pressure within the aneurysm sac to determine whether the intervention is leaking. The standard treatment for AAAs employs the use of stent-grafts that are implanted via endovascular techniques. However, a significant problem that has emerged with these stent-grafts for AAAs is acute and late leaks of blood into the aneurysms sac. Currently, following stent-graft implantation, patients are subjected to periodic evaluation via abdominal CT (Computed Tomography) with IV contrast to identify the potential presence of stent-graft leaks. This is an expensive, risky procedure that lacks appropriate sensitivity to detect small leaks.

Typically, the sensors utilize an inductive-capacitive ("LC") resonant circuit with a variable capacitor. The capacitance of the circuit varies with the pressure of the environment in which the sensor is located and thus, the resonant frequency of the circuit varies as the pressure varies. Accordingly, the resonant frequency of the circuit can be used to calculate pressure.

Ideally, the resonant frequency is determined using a non-invasive procedure. Several examples of procedures for determining the resonant frequency of an implanted sensor are discussed in U.S. Pat. No. 6,111,520. Some of the procedures described in the patent require the transmission of a signal having multiple frequencies. A drawback of using a transmission signal having multiple frequencies is that the energy in the frequency bands outside the resonant frequency is wasted. This excess energy requires more power which results in an increase in cost, size, and thermal requirements, as well as an increase in electromagnetic interference with other signals. Thus, there is a need for an optimized method that is more energy efficient and requires less power.

There are unique requirements for communicating with an implanted sensor. For example, the system must operate in a low power environment and must be capable of handling a signal from the sensor with certain characteristics. For example, the signal from the sensor is relatively weak and must be detected quickly because the signal dissipates quickly. These requirements also impact the way that common problems are handled by the system. For example, the problems of switching transients and false locking need to be handled in a manner that accommodates the sensor signal characteristics. Thus, there is a need for a method for communicating with a wireless sensor that operates in a low power environment and that efficiently determines the resonant frequency of the sensor.

The resonant frequency of the sensor is a measured parameter that is correlated with the physical parameter of interest. To be clinically useful there must be means to ensure that variations in measurement environment do not affect the accuracy of the sensor. Thus, there is a need for a system and method for communicating with a wireless sensor that considers variations in the measurement environment.

SUMMARY OF THE INVENTION

The primary goal of aneurysm treatment is to depressurize the sac and to prevent rupture. Endoleaks, whether occurring intraoperatively or postoperatively, can allow the aneurysmal sac to remain pressurized and therefore, increase the chance of aneurysm rupture. The current imaging modalities angiography and CT scan are not always sensitive enough to detect endoleaks or stent graft failure. Intrasac pressure measurements provide a direct assessment of sac exclusion from circulation and may therefore offer intraoperative and post operative surveillance advantages that indirect imaging studies do not.

In one application of the present invention, a AAA pressure sensor is placed into the aneurysm sac at the time of stent-graft insertion. The pressure readings are read out by the physician by holding an electronic instrument, which allows an immediate assessment of the success of the stent-graft at time of the procedure and outpatient follow-up visits, by reading the resonant frequency of the wireless sensor and correlating the frequency reading to pressure.

The present invention meets the needs described above by providing a system and method for communicating with a wireless sensor to determine the resonant frequency of the sensor. The system energizes the sensor with a low duty cycle, gated series of bursts of RF energy, or energizing signals, having predetermined frequencies or set of frequencies and a predetermined amplitude. In one embodiment, the energizing signal is transmitted in sets of three bursts. The first of the three bursts has a predetermined frequency that is below an estimate, at the time, of the sensor's resonant frequency. The second of the three bursts has a predetermined frequency at the estimate, at the time, of the sensor's resonant frequency. The third of the three bursts is at a predetermined frequency above the estimate, at the time, of the sensor's resonant frequency.

The energizing signals are coupled to the sensor via a magnetic loop. The sensor may be an inductive-capacitive ("LC") resonant circuit with a variable capacitor that is implanted within the body and used to measure physical parameters, such as pressure or temperature. At least one of the energizing signals induces a current in the sensor which is maximized when the energizing frequency is the same as the resonant frequency of the sensor. The system receives the ring down response of the sensor via magnetic coupling for each of the three energizing signals and determines the resonant frequency of the sensor, which is used to calculate the measured physical parameter.

In one aspect of the invention, the system uses a group phase delay measurement to adjust the frequency of the energizing signals until the system locks to or identifies the resonant frequency of the sensor. In one embodiment, three ring down, or sensor, signals from the sensor, each corresponding to an energizing signal, are received and the phases of each signal are measured. The phase difference between the first and second signal is determined as a first group phase delay. The phase difference between the second and third signal is determined as a second group phase delay. For example, the phase of the first sensor signal is subtracted from the phase of the second sensor signal to determine the first group phase delay. Similarly, the phase of the second sensor signal is subtracted from the phrase of the third sensor signal to determine the second group phase delay.

The first group phase delay and second group phase delay are compared. Based on the comparison, the system may lock on the resonant frequency of the sensor or adjust a subsequent set of three energizing signals. For example, the first group phase delay can be subtracted from the second group phase delay. If the difference between the first group phase delay and second group phase delay is zero, then the system locks on the resonant frequency of the sensor at the frequency of the second energizing signal. If the difference between the first group phase delay and second group phase delay is positive, the frequencies of next set of transmitted energizing signals may be adjusted higher. If the difference between the first group phase delay and second group phase delay is negative, the frequencies of the next set of transmitted energizing signals may be adjusted lower.

In some embodiments of the present invention, the system performs a calibration cycle before performing a measurement to determine the resonant frequency of the wireless sensor. For example, the system may transmit a calibration signal having a reference phase. The system receives at least a portion of the calibration, measures the phase of the received signal, and adjusts the phase of a subsequently transmitted calibration signals until the transmitted phase and the received phase are the same.

In some embodiments of the present invention, a digital signal processor (DSP) can be used to perform the group phase delay determination and/or during the calibration cycle to correct for delays in the system components. For example, the DSP can measure the phase of each of the sensor signals, determine the group phase delay values, and compare the group phase delay values. Based on the comparison, the DSP can control the frequency of a subsequent set of energizing signals.

These and other aspects, features and advantages of the present invention may be more clearly understood and appreciated from a review of the following detailed description of the disclosed embodiments and by reference to the appended drawings and claims.

DETAILED DESCRIPTION

The present invention is directed towards a system and method for communicating with a wireless sensor. Briefly described, the present invention determines the resonant frequency of the sensor by adjusting the phase and frequency of one or more energizing signals until the frequency of this signal locks to the resonant frequency of the sensor. The frequency of the energizing signal can be adjusted using a group phase delay operation. The system energizes the sensor with a low duty cycle, gated burst of RF energy at a predetermined set of frequencies and a predetermined amplitude. In some embodiments, the set of frequencies includes three different energizing signals at different frequencies which are transmitted separately. The signals induce current in the sensor that can be used to track the resonant frequency of the sensor. The system receives the ring down response of the sensor as sensor signals at three different frequencies and determines the resonant frequency of the sensor from phase measurements. The resonant frequency can be used to calculate a measured physical parameter.

Exemplary System

Figure 1:
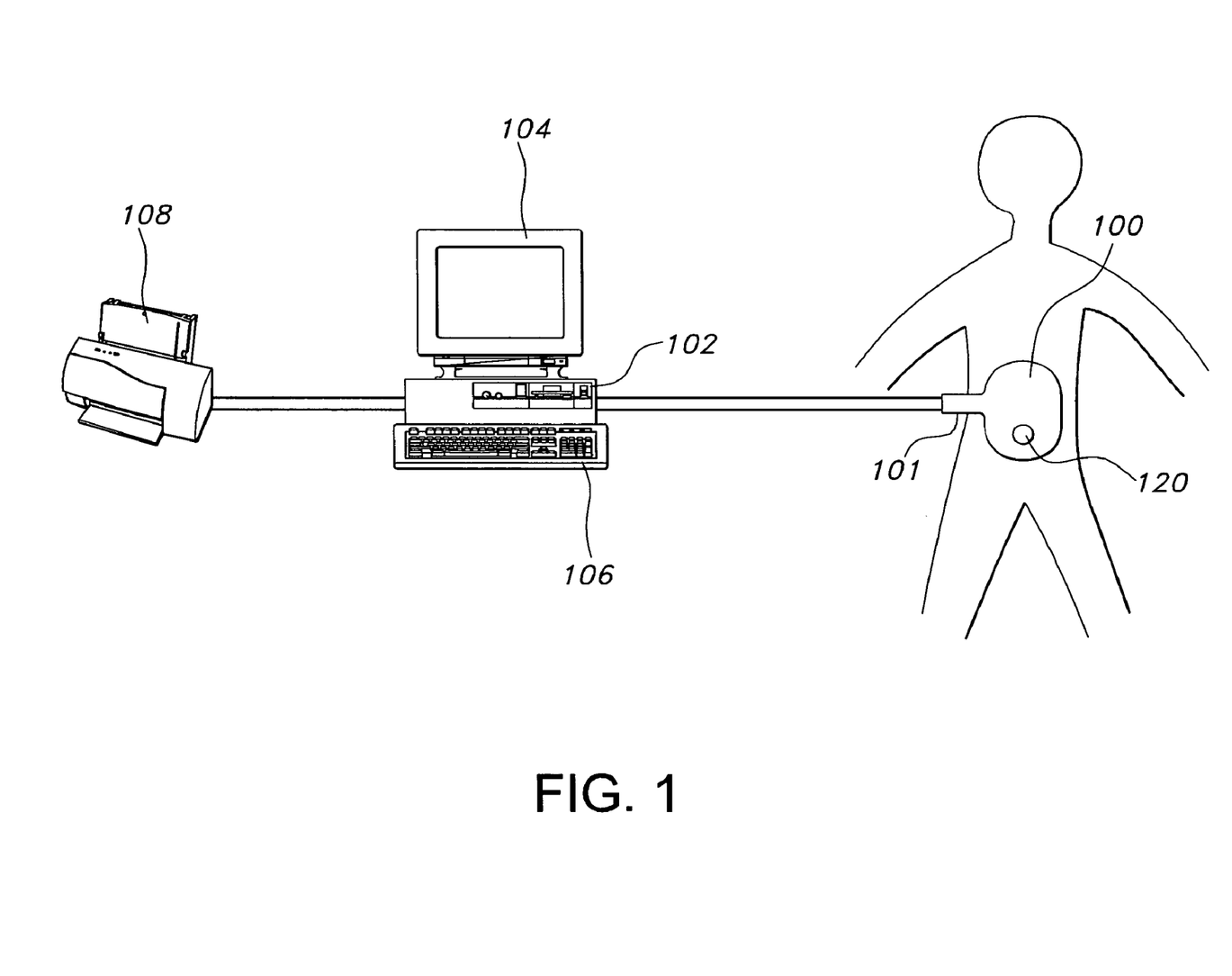
FIG. 1 is a block diagram of an exemplary system for communicating with a wireless sensor in accordance with an embodiment of the invention.

FIG. 1 illustrates an exemplary system for communicating with a wireless sensor implanted within a body. The system includes a coupling loop 100, a base unit 102, a display device 104 and an input device 106, such as a keyboard.

The coupling loop is formed from a band of copper. In one embodiment, the loop is eight inches in diameter. The coupling loop includes switching and filtering circuitry that is enclosed within a shielded box 101. The loop charges the sensor and then couples signals from the sensor into the receiver. The antenna can be shielded to attenuate in-band noise and electromagnetic emissions.

Figure 3:
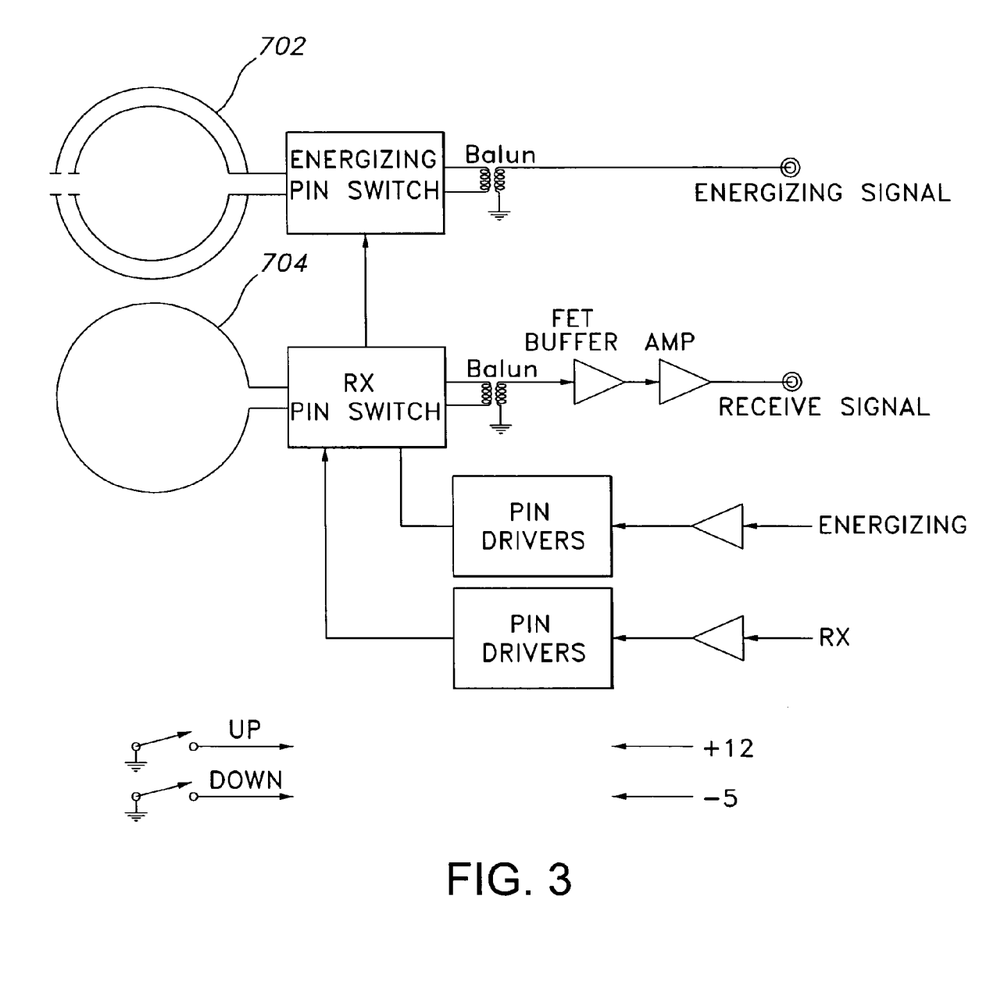
FIG. 3 is a block diagram of an exemplary antenna system for communicating with a wireless sensor in accordance with an embodiment of the invention.

Another possible embodiment for a coupling loop is shown in FIG. 3, which shows separate loops for energizing 702 and for receiving 704, although a single loop can be used for both functions. PIN diode switching inside the loop assembly is used to provide isolation between the energizing phase and the receive phase by opening the RX path pin diodes during the energizing period, and opening the energizing path pin diodes during the coupling period. Multiple energizing loops can be staggered tuned to achieve a wider bandwidth of matching between the transmit coils and the transmit circuitry. Examples of coupling loops are disclosed in U.S. patent application Ser. No. 11/479,527, entitled "Coupling Loop and Method for Positioning Coupling Loop," incorporated herein by reference.

The base unit includes an RF amplifier, a receiver, and signal processing circuitry. Additional details of the circuitry are described below in connection with FIG. 10.

The display 104 and the input device 106 are used in connection with the user interface for the system. In the embodiment illustrated in FIG. 1 the display device and the input device are connected to the base unit. In this embodiment, the base unit also provides conventional computing functions. In other embodiments, the base unit can be connected to a conventional computer, such as a laptop, via a communications link, such as an RS-232 link. If a separate computer is used, then the display device and the input devices associated with the computer can be used to provide the user interface. In one embodiment, LABVIEW software is used to provide the user interface, as well as to provide graphics, store and organize data and perform calculations for calibration and normalization. The user interface records and displays patient data and guides the user through surgical and follow-up procedures.

An optional printer 108 is connected to the base unit and can be used to print out patient data or other types of information. As will be apparent to those skilled in the art other configurations of the system, as well as additional or fewer components can be utilized with the invention.

Patient and system information can be stored within a removable data storage unit, such as a portable USB storage device, floppy disk, smart card, or any other similar device. The patient information can be transferred to the physician's personal computer for analysis, review, or storage. An optional network connection can be provided to automate storage or data transfer. Once the data is retrieved from the system, a custom or third party source can be employed to assist the physician with data analysis or storage.

FIG. 1 illustrates the system communicating with a sensor 120 implanted in a patient. The system is used in two environments: 1) the operating room during implant and 2) the doctor's office during follow-up examinations. During implant the system is used to record at least two measurements. The first measurement is taken during introduction of the sensor for calibration and the second measurement is taken after placement for functional verification of the stent graft. The measurements can be taken by placing the coupling loop either on or adjacent to the patient's back or the patient's stomach for a sensor that measures properties associated with an abdominal aneurysm. For other types of measurements, the coupling loop may be placed in other locations. For example, to measure properties associated with the heart, the coupling loop can be placed on the patient's back or the patient's chest.

The system communicates with the implanted sensor to determine the resonant frequency of the sensor. As described in more detail in the patent documents referenced in the Background section, a sensor typically includes an inductive-capacitive ("LC") resonant circuit having a variable capacitor. The distance between the plates of the variable capacitor varies as the surrounding pressure varies. Thus, the resonant frequency of the circuit can be used to determine the pressure.

Figure 5:
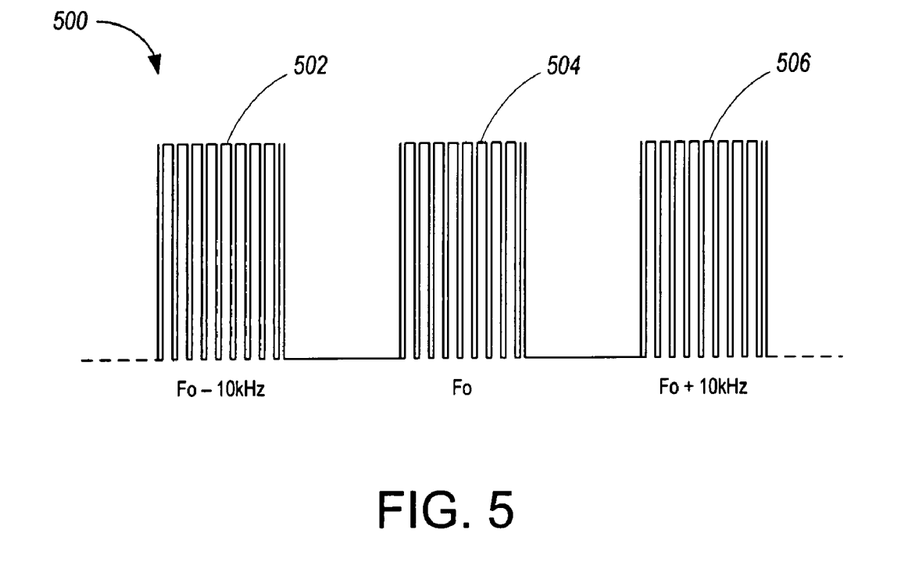
FIG. 5 is a graph illustrating a set of exemplary energizing signals according to one embodiment of the invention.

The system energizes the sensor with a series of RF bursts. The RF bursts include a set of three energizing signals that can be transmitted as low duty cycle, gated bursts of RF energy of predetermined frequencies and predetermined amplitudes. FIG. 5 illustrates a set 500 of energizing signals having three different frequencies that may be transmitted by the system. The frequencies of the energizing signals are separated by a predetermined frequency. In the embodiment illustrated in FIG. 5, the energizing signals are separated by 10 kHz. The first energizing signal 502 has a frequency of 10 kHz less than an estimate, at the time of transmission, of the wireless sensor resonant frequency. The second energizing signal 504 has a frequency at the estimated wireless sensor resonant frequency. The third energizing signal 506 has a frequency of 10 kHz greater than the estimated wireless sensor resonant frequency. The estimate of the wireless sensor resonant frequency may be based on a number of factors, including but not limited to, typical resonant frequencies of similar wireless sensors, previously determined resonant frequencies of the particular wireless sensor, environmental conditions, measurement distance, or other measurement factors. In some embodiments, the amplitudes of the energizing signals are the same. In other embodiments, the amplitudes can be different.

Typically, the three energizing signals are transmitted at a frequency between 30-37.5 MHz, but may be any frequency capable of exciting the wireless sensor. In the embodiment shown in FIG. 5, the transmit bursts for each energizing signal is 2 us and the idle time between each energizing signal is 3 us.

Figure 2A:
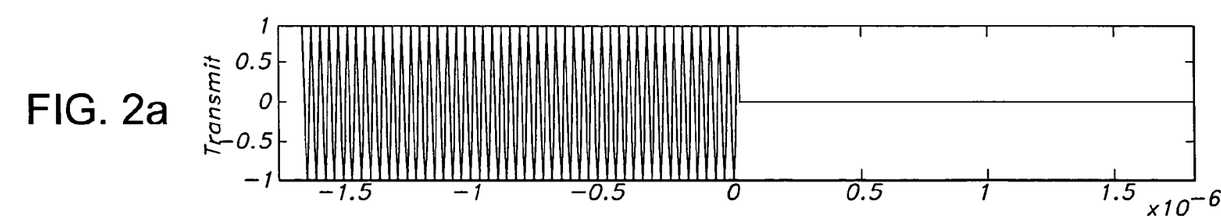
FIG. 2(a) is a graph illustrating an exemplary energizing signal in accordance with an embodiment of the invention.
Figure 2B:
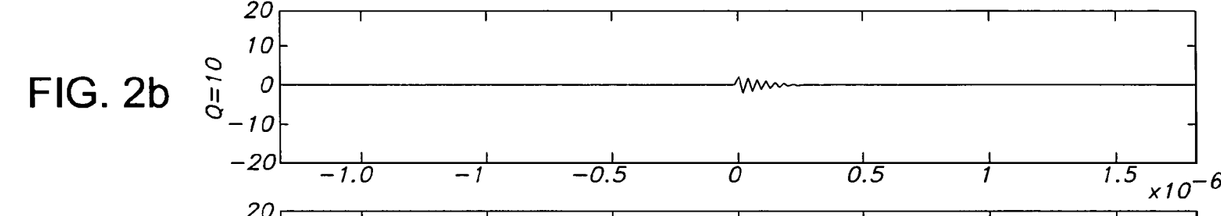
FIGS. 2(b), 2(c) and 2(d) are graphs illustrating exemplary coupled signals in accordance with an embodiment of the invention.
Figure 2C:
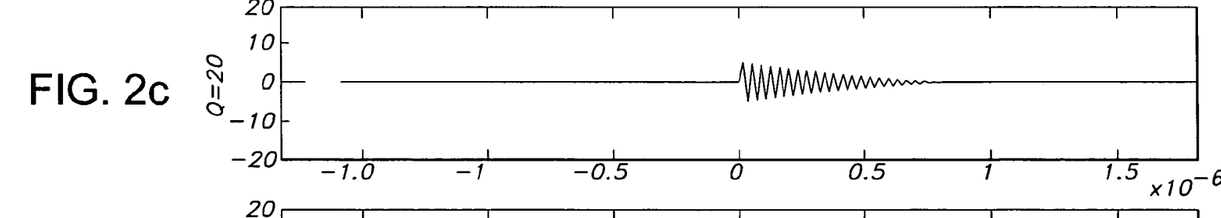
Figure 2D:
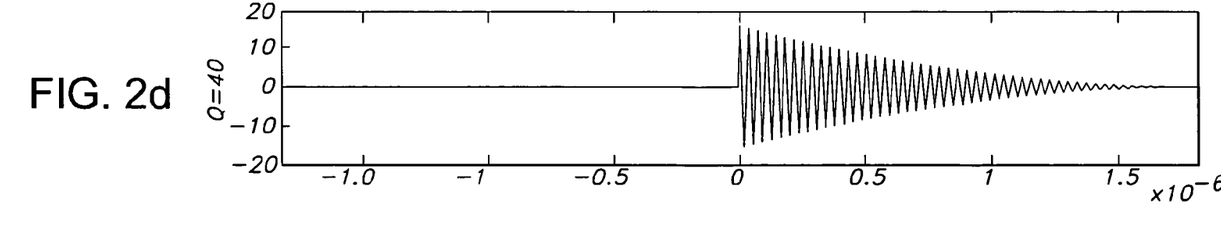
Figure 4:
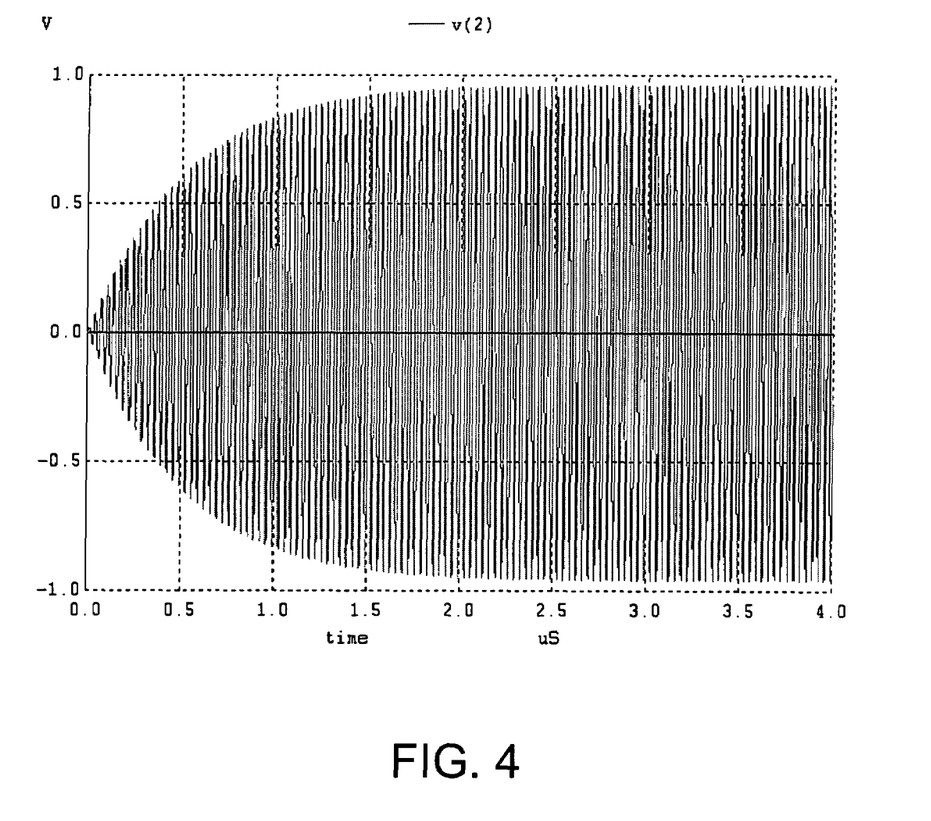
FIG. 4 is a graph illustrating an exemplary charging response of an LC circuit in accordance with an embodiment of the invention.

Each of the energizing signals are coupled to the sensor via a magnetic loop. These signals induce a current in the sensor which has maximum amplitude at the resonant frequency of the sensor. During this time, the sensor charges exponentially to a steady-state amplitude that is proportional to the coupling efficiency, distance between the sensor and loop, and the RF power. FIG. 4 shows the charging response of a typical LC circuit to a burst of RF energy at its resonant frequency. The speed at which the sensor charges is directly related to the Q (quality factor) of the sensor. FIG. 2(a) illustrates one energizing signal that may be transmitted in a set and FIGS. 2(b), 2(c) and 2(d) illustrate typical coupled signals for various values of Q (quality factor) for the sensor. When the main unit is coupling energy at or near the resonant frequency of the sensor, the amplitude of the sensor return is maximized, and the phase of the sensor return will be close to zero degrees with respect to the energizing phase. Therefore, the "on time" of the pulse repetition duty cycle is optimized for the Q of the sensor.

Figure 6:
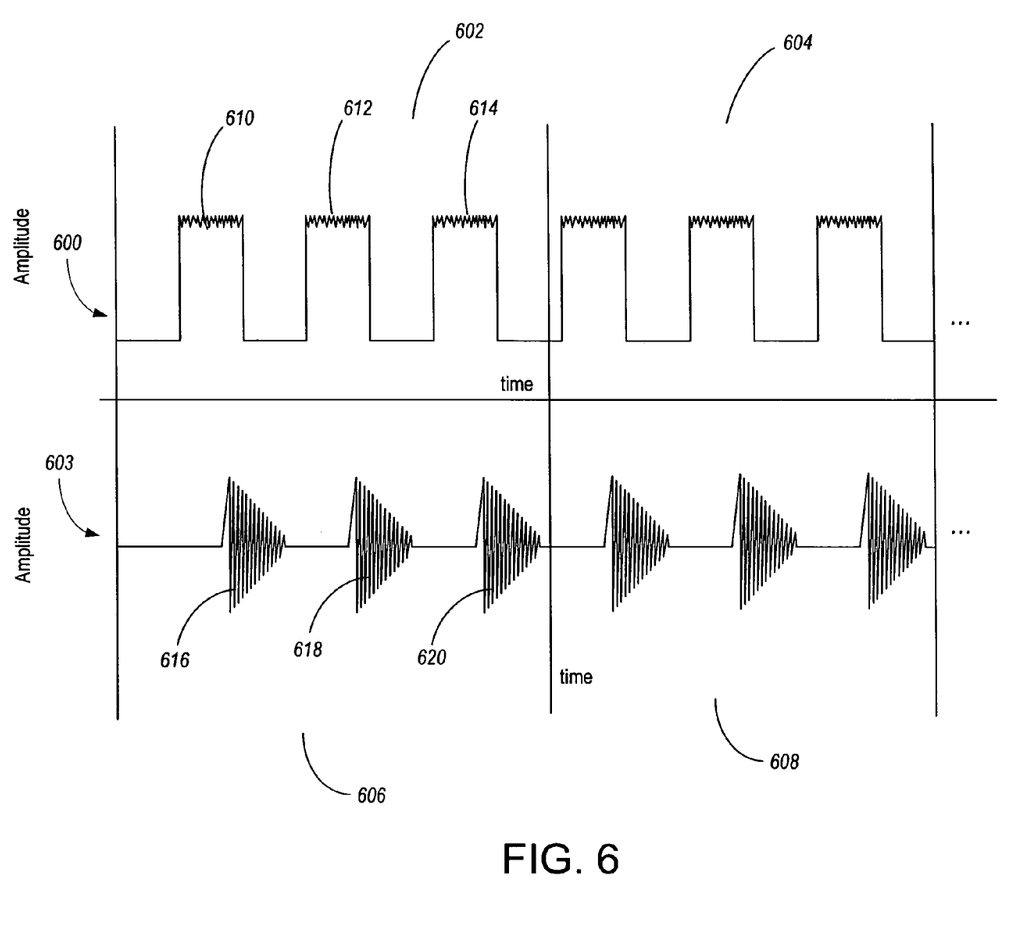
FIG. 6 is a graph illustrating exemplary energizing signals and corresponding sensor signals according to one embodiment of the invention.

FIG. 6 illustrates amplitudes of energizing signals 600 and sensor signals 603 with respect to time in accordance with one embodiment of the present invention. The energizing signals 600 include a first set 602 and a second set 604. Similarly, the sensor signals include a first set 606 corresponding to first set 602 of energizing signals 600 and a second set 608 corresponding to the second set 604 of energizing signals 600. The first set 602 of energizing signals include a first energizing signal 610 having a frequency below an estimation of the resonant frequency of the wireless sensor, a second energizing signal 612 having a frequency at the estimation of the resonant frequency, and a third energizing signal 614 having a frequency above the estimation of the resonant frequency. The energizing signals are each transmitted for a predetermined duration. The energizing signals cause the wireless sensor to resonant and ring down a sensor signal that is received by the system. For example, sensor signal 616 is a ring down response to energizing signal 610, sensor signal 618 is a ring down response to energizing signal 612, and sensor signal 620 is a ring down response to energizing signal 614. Each of the sensor signals 616, 618, 620 have a phase that is measured by the system. The system can use the phase information for each of the sensor signals 616, 618, 620 to determine a resonant frequency of the wireless sensor.

Figure 7:
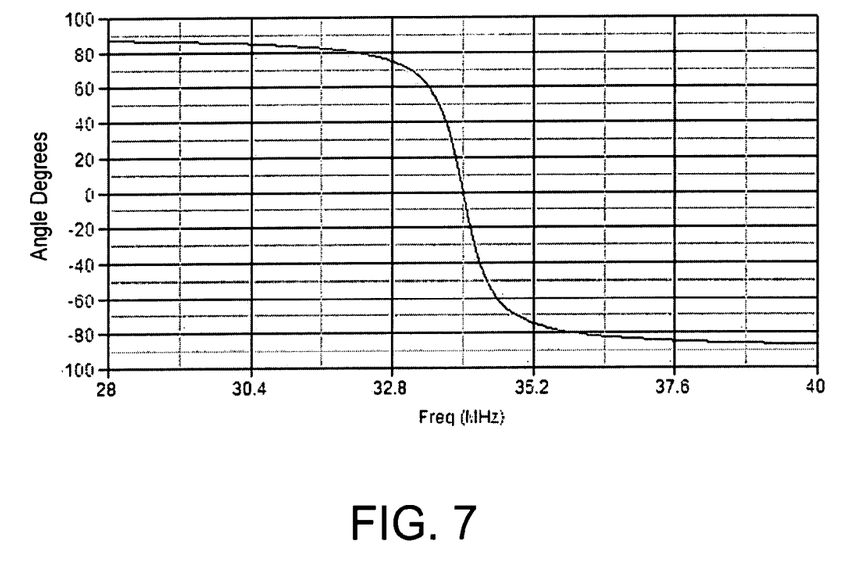
FIG. 7 is a graph illustrating an exemplary phase slope of a sensor signal according to one embodiment of the invention.

The system receives the ring down response of the sensor for each of the three energizing signals via magnetic coupling. The phase of the wireless sensor signal various most rapidly at or near the wireless resonant frequency. FIG. 7 shows a phase response for a wireless sensor having a resonant frequency between 32.8 MHz and 35.2 MHz and a Q of approximately 50. In particular, the resonant frequency is at the point having a maximum phase slope.

Each of the three sensor signals corresponds to an energizing signal in the set. For example, a first sensor signal is a ring down response from the wireless sensor for the first energizing signal, a second sensor signal is a ring down response from the wireless sensor for the second energizing signal, and the third sensor signal is a ring down response from the wireless sensor for the third energizing signal. A phase for each sensor signal is measured. The sensor signals may be down converted to an intermediate frequency (IF) before measuring phase values for each sensor signal before processing. For example, the receiver oscillator may be set at a predetermined frequency above the second energizing signal frequency. In one embodiment, the receiver oscillator is 20 kHz above the second energizing signal frequency. When converting the received signals to an IF, the sensor signals are mixed with the local oscillator and are passed through a low-pass filter that results in the signals at the IF. The signals are then processed by the system, such as by a DSP. In other embodiments, phase measurement is performed on the sensor signal without down conversion. The phase for each sensor signal may also be adjusted to compensate for known error sources. Using the Q for the sensor and the phase measurement for each of the three sensor signals, the system can adjust the frequencies of a subsequent set of energizing signals and/or determine the resonant frequency of the sensor by processing the sensor signals using a group phase delay.

Group phase delay may include determining two group phase delay values using the phase of each of the sensor signals and comparing the two group phase delay values. The phase measurement for the first sensor signal is subtracted from the phase measurement for the second sensor signal to generate the first group phase delay value. The phase measurement of the second sensor signal is subtracted from the phase measurement of the third sensor signal to generate the second group phase delay value. The first group phase delay value is compared to the second group phase delay value. For example, the first group phase delay value may be subtracted from the second group phase delay value.

Figure 8:
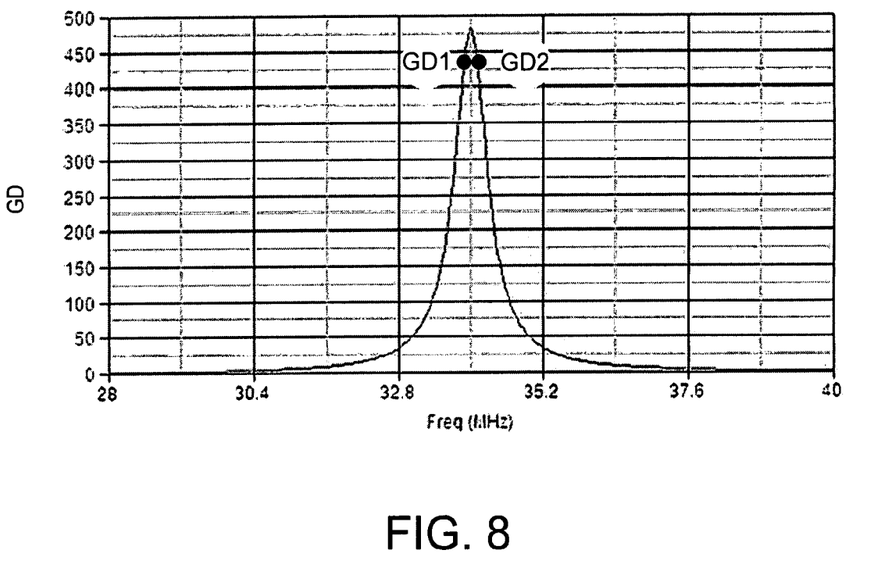
FIG. 8 is a graph illustrating calculated group delays in a locked state according to one embodiment of the invention.

If the comparison of the group phase delay values result is zero, the system has locked on the resonant frequency of the wireless sensor, which is equal to the second energizing signal. FIG. 8 shows a graph of the group phase delay values in an identified or locked state. In particular, FIG. 8 shows a first group phase delay (GD1) and a second group phase delay (GD2) plotted on a graph of normalized group delay values with respect to frequency of the energizing signals. The graph also includes a line 700 of the expected group phase delay values.

Figure 9:
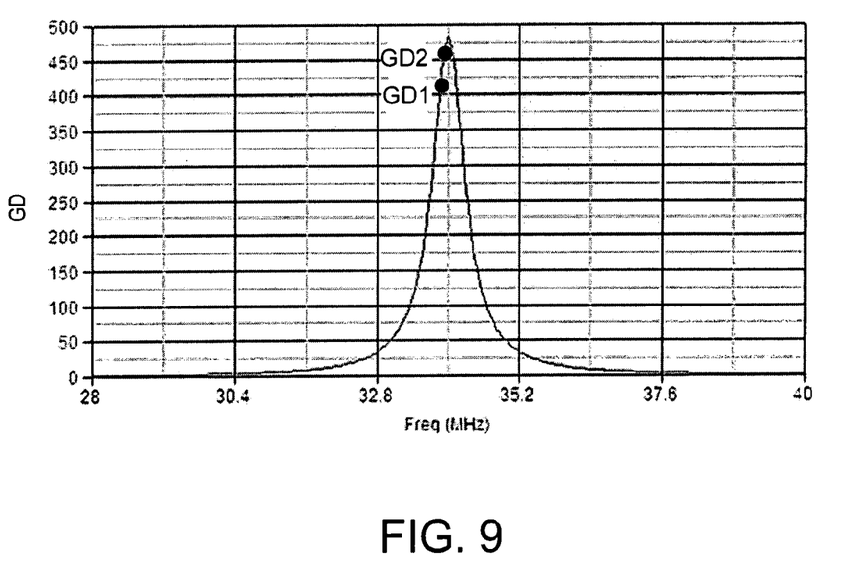
FIG. 9 is a graph illustrating calculated group delays in an un-locked state according to one embodiment of the invention.

If the comparison of the group phase delay values results in a positive or negative value, the system adjusts the energizing signals in a subsequent set of energizing signals accordingly. For example, if the comparison of the group values result is positive, as shown in FIG. 9, the system increases the frequencies of the next set of energizing signals. FIG. 9 shows a graph of a first group phase delay (GD1) and second group phase delay (GD2). GD2 is greater than GD1 and thus the group phase delay comparison result is positive. If the comparison of the group phase delay values result is negative, the system decreases the frequencies of the next set of energizing signals.

If the group phase delay comparison does not result in a lock on the resonant frequency of the wireless sensor, the process may be repeated, as necessary, until a lock is obtained.

False Locks

Embodiments of the present invention may be utilized in an environment, such as a surgical environment, that may include room resonance, such as devices having a resonant frequency in a similar range of the wireless sensor. Interrogators may lock on the room resonance, providing a false lock. The group phase delay determined from the received signals may be used to reject most, if not all, of the false locks. For example, the group phase delay is related to the Q of a resonant device by the following relationship:

$$GD = 2 \cdot \frac{Q}{\omega}$$

In the above relationship, $\omega$ to is the locked resonant frequency and GD is the group phase delay. If the Q of the wireless sensor, or an approximate value, is known and the group phase delay value and frequency of the received signal is determined, false locks may be determined and rejected by determining the Q using the group phase delay value and frequency. For example, the locked resonant frequency of a resonating device and the group phase delay can be determined using group phase delay. The Q for the resonating device may be determined using the following relationship. The determined Q is then compared to the known value, or best estimate, of the Q of the wireless sensor. If the Qs do not match, the lock is a false lock and ignored by the system. In some embodiments of the present invention, the Q value for the wireless sensor is 50, but the Q value may be affected by the environment surrounding the wireless sensor. For example, the proximity of the wireless sensor to the stent may alter the Q value.

Operation of the Base Unit

Figure 10:
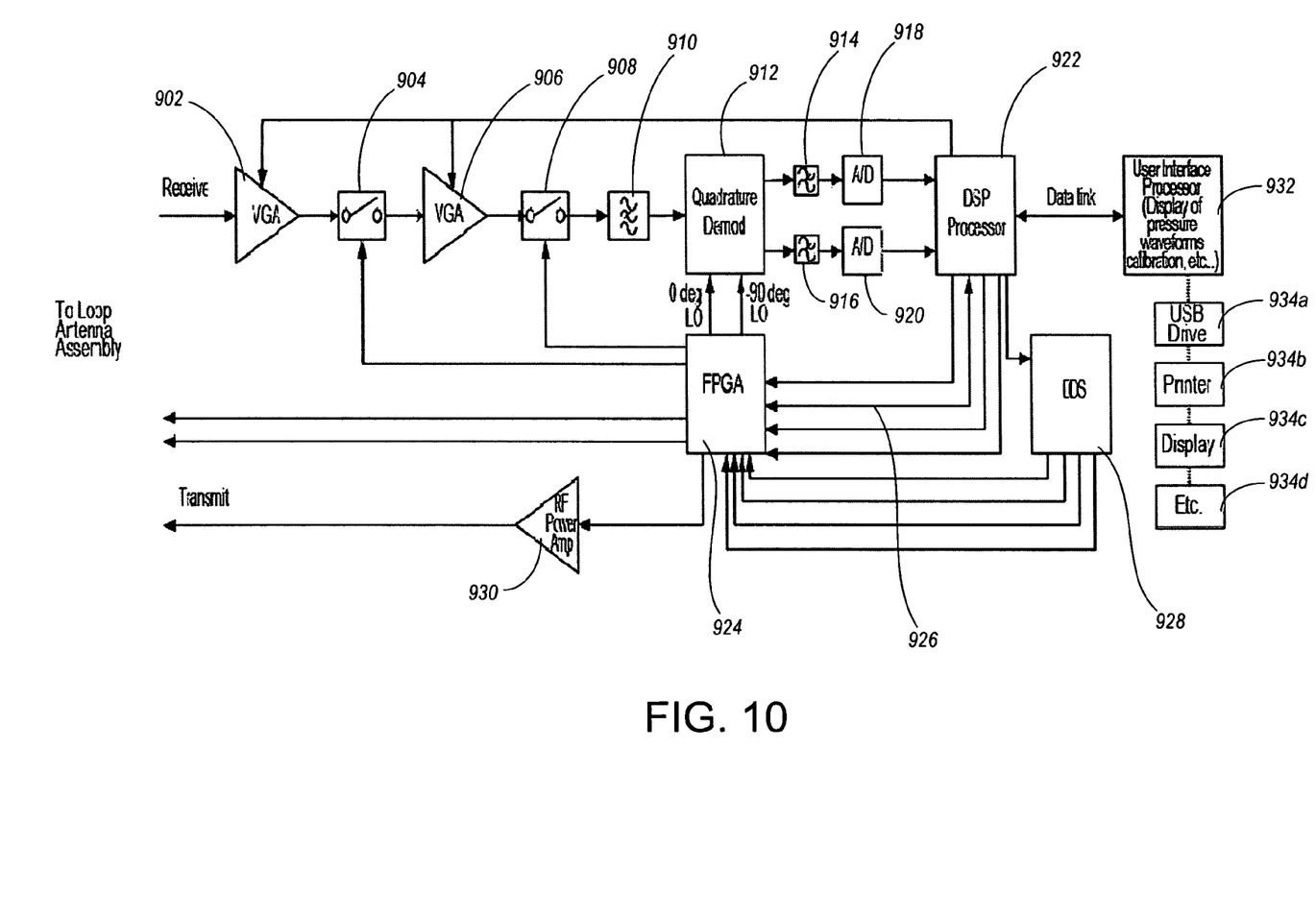
FIG. 10 is a block diagram of an exemplary base unit in accordance with an embodiment of the invention.

FIG. 10 is a block diagram of the signal processing components of an exemplary base unit 900. The base unit determines the resonant frequency of the sensor by finding the group phase delay of the received signals and adjusting the energizing signals so that the frequency of the second energizing signal of a transmitted set of energizing frequencies matches the resonant frequency of the sensor. After the base unit transmits each energizing signal in a set of three energizing signals, it receives the resulting sensor signal and processes the received signals to lock the resonant frequency of the wireless sensor. In the embodiment illustrated by FIG. 10, sensor signals are received in front end components that may include an amplifier, such as variable gain amplifier 902 to amplify the received sensor signals. An analog switch 904 may be provided to open when the system is transmitting and close when the system receives to prevent transmitted signals from being processed. Due to the weak signals received, a second variable gain amplifier 906 is provided to further amplify the weak received sensor signals.

A second switch 908 may also be provided to further prevent energizing signals from being received by the receiver components. In particular, energizing signals may affect a filter 910 by charging the filter and corrupting the performance of the filter 910 unless preventive components, such as switch 908, are included. The filter 910 may be a band-pass filter to reduce the sensitivity of the system to out-of-band signals and limit the noise bandwidth associated with the system before the sensor signals are demodulated.

The filtered sensor signals are then input into a demodulator, such as quadrature demodulator 912. The quadrature demodulator 912 mixes the received signal with two local oscillators, 90 degrees apart in phase, at the same frequency as the received signal. The result of mixing is two baseband signals, together providing a vector representation of the pre-demodulated signal, where one baseband signal represents the magnitude and the other baseband signal represents the phase. The demodulated baseband signals are then passed through low-pass filters 914, 916 respectively. The low-pass filters 914, 916 filter any carrier signals that may remain and act as anti-aliasing filter before the analog-to-digital sampling process.

Analog-to-digital converters 918, 920 may be provided to convert the analog baseband signals to a digital format for processing with DSP 922. In some embodiments, the DSP 922 includes analog-to-digital converters 918, 920. The DSP 922 can perform the group phase delay determination. In some embodiments, the DSP 922 can be configured to perform other error methods that may be used to determine the resonant frequency of the wireless sensor. For example, the DSP 922 may be used to process and adjust a phase of a transmitted signal to make the phase between a received calibration signal and the received sensor signal the same, as disclosed in U.S. patent application Ser. No. 11/276,571. The DSP 922 may be configured to operate in group phase delay mode and another mode at the same or different time.

For group phase delay, the DSP 922 measures the phase of the baseband signals for each of the three received sensor signals in a set. The DSP 922 then computes a first group phase delay value by subtracting the phase of the first sensor signal from the phase of the second sensor signal and the second group phase delay value by subtracting the phase of the second sensor signal from the phase of the third sensor signal. The DSP 922 then compares the two group phase delay values by subtracting the first group phase delay value from the second group phase delay value. If the value is zero, the DSP 922 can determine the resonant frequency of the wireless sensor using the frequency of the second energizing signal. If the value is positive, the DSP 922 can adjust the frequency of the energizing signals transmitted in a subsequent set higher than those in the previous set. If the value is negative, the DSP 922 can adjust the frequency of the energizing signals transmitted in the subsequent set lower than those in the previous set.

The DSP 922 may be in communication with a user interface 932 that is associated with one or more peripheral devices 934a-d. The DSP 922 can convert the phase of the second received sensor signal to a pressure reading and cause the pressure reading to be displayed numerically and/or graphically on the user interface 932 and/or stored in an electronic storage medium.

The DSP 922 may access a field-programmable gate array (FPGA) 924 to, among other things, read/write data to a register bank in the FPGA 924. The register bank may include 32 16-bit registers and the DSP 922 can modify the timing of the transmitted sets of energizing signals via the registers. In some embodiments, the FPGA 924 provides for up to 8 different energizing signal types to be defined. The different energizing signal types may have different phase and/or frequencies. In one embodiment, six signal types are utilized: 3 different frequency offsets and a calibration signal for each. The DSP 922 can select the type of energizing signals to include in a subsequent set via a 3-bit wide set of control lines 926 between the DSP 922 and FPGA 924 based on the results of the group phase delay comparisons. By providing signal selection capabilities of the DSP 922, the timing of the analog-to-digital conversion stage in accordance with arriving sensor signals may be simplified and transmit power may be conserved by reducing pulse repetitions.

When the DSP 922 directs the FPGA 924 to transmit an energizing signal, the FPGA 924 may set a switch on an antenna PIN diode switch to transmit mode, send the energizing signal to an RF power amplifier 930, change the antenna PIN diode switch to receive mode, and open the receive switches 904, 908. The power amplifier 930 may be a MOSFET amplifier that is driven by the FPGA 924 and sends an energizing signal with the appropriate transmit power to the antenna via coaxial cable.

The DSP 922 and FPGA 924 may be in communication with a direct digital synthesizer (DDS) 928. For example, the DSP 922 can control the DDS 928, which generates local oscillator signals. The DDS 928 may be a multi-channel digitally tuned oscillator with frequency and phase controlled by the DSP 922. In some embodiments, the DDS 928 includes two output channels. If only two channels are utilized, the outputs are at the same frequency, but have a phase difference of 90 degrees. The DSP 922 can dynamically change the frequency of both channels for each energizing signal set. In other embodiments, 4 channels are utilized with 3 channels configured for each of the three energizing signals in a set and the fourth channel configured as a dynamically tuned local oscillator with a 90 degree phase shift with respect to the energizing signal set.

The FPGA 924 may also direct the appropriate DDS input to local oscillator ports associated with the quadrature demodulator 912 and a gated version of a local oscillator at 0 degree phase to the RF power amplifier 930 as a transmit frequency.

In other embodiments of the base unit 900, the received sensor signals are demodulated by quadrature demodulation in the FPGA 924 by applying an IF signal to one analog-to-digital converter and removing the second analog-to digital converter and associated filter. Alternatively, the amplified sensor signals may be applied directly to an analog-to-digital converter without demodulation.

Additional alternative embodiments will be apparent to those skilled in the art to which the present invention pertains without departing from its spirit and scope. For example, the system can operate with different types of sensors, such as non-linear sensors that transmit information at frequencies other than the transmit frequency or sensors that use back-scatter modulations. Furthermore, sets of energizing signals may include more than three signals. The partition of system functions between the DSP, FPGA, DDS, and quadrature demodulator are merely exemplary and the functions may be performed any one or combination of the disclosed components, as well as other components. Accordingly, the scope of the present invention is described by the appended claims and is supported by the foregoing description.

What is claimed is:

1. A method for determining a resonant frequency of a wireless sensor, comprising:
    generating a first set of energizing signals, wherein the first set of energizing signals comprises a plurality of energizing signals, each with a different frequency;
    receiving a first set of sensor signals, wherein each sensor signal corresponds to one of the energizing signals;
    determining a phase for each of the sensor signals in the first set of sensor signals;
    determining a first group phase delay and a second group phase delay using the phases of the sensor signals;
    comparing the first group phase delay to the second group phase delay; and determining the resonant frequency of the wireless sensor based on the group phase delay comparison.

2. The method of claim 1, wherein the first set of energizing signals comprises:
a first energizing signal having a first frequency below an estimation of the resonant frequency of the wireless sensor;
a second energizing signal having a second frequency at the estimation of the resonant frequency; and
a third energizing signal having a third frequency above the second frequency.

3. The method of claim 2, further comprising:
generating a second set of energizing signals, the second set of energizing signals comprising:
a first energizing signal having a first frequency below a second frequency;
a second energizing signal having the second frequency; and
a third energizing signal having a third frequency above the second frequency; and
selecting the second frequency of the second set based on the group phase delay comparison.

4. The method of claim 3, further comprising:
selecting the first frequency of the second set and the third frequency of the second set based on the group phase delay comparison.

5. The method of claim 3, wherein selecting the second frequency of the second set comprises:
selecting the second frequency of the second set as a higher frequency than the second frequency of the first set if the group phase delay comparison is positive; and
selecting the second frequency of the second set as a lower frequency than the second frequency of the first set if the group phase delay comparison is negative.

6. The method of claim 1, wherein the first frequency and third frequency are offset from the second frequency by a predetermined amount.

7. The method of claim 1, wherein comparing the first group phase delay and the second group phase delay comprises subtracting the first group phase delay from the second group phase delay.

8. The method of claim 1, further comprising:
receiving a calibration signal during a calibration cycle;
processing the calibration signal during a first period within the calibration cycle to create an IF calibration signal;
determining a first phase difference between the IF calibration signal and a reference signal; and
based on the first phase difference adjusting the phases of the energizing signals to reduce the first phase difference.

9. The method of claim 1, wherein determining the resonant frequency of the wireless sensor based on the group phase delay comparison comprises:
selecting a second energizing signal of a subsequent set of energizing signals until the group phase delay comparison results in zero.

10. A method for determining a resonant frequency of a wireless sensor, comprising:
receiving a first sensor signal having a first phase;
receiving a second sensor signal having a second phase;
receiving a third sensor signal having a third phase;
generating a first group phase delay by subtracting the first phase from the second phase;
generating a second group phase delay by subtracting the second phase from the third phase;
comparing the first group phase delay to the second group phase delay by subtracting the first group phase delay from the second group phase delay; and
based on the group phase delay comparison, determining the resonant frequency of the wireless sensor.

11. The method of claim 10, further comprising:
selecting an energizing signal frequency based on the group phase delay comparison.

12. The method of claim 11, further comprising:
receiving a calibration signal;
processing the calibration signal to create an IF calibration signal;
determining a first phase difference between the IF calibration signal and a reference signal; and
based on the first phase difference selecting the phase of the energizing signal to reduce the first phase difference.

13. The method of claim 12, wherein selecting a phase of an energizing signal is repeated until the first phase difference between the IF calibration signal and the reference signal corresponds to a first predetermined value.

14. The method of claim 11, further comprising:
using the resonant frequency of the sensor to determine a physical parameter associated with the sensor.

15. A system for determining a resonant frequency of a wireless sensor, comprising:
a base unit for transmitting a first set of energizing signals and receiving a first set of sensor signals, wherein each of the energizing signals of the first set has a different frequency and each of the sensor signals of the first set has a phase;
wherein the base unit comprises a signal processor for measuring the phase for each of the sensor signals, determining a first group phase delay and a second group phase delay based on the sensor signal phases, comparing the first group phase delay and second group phase delay, and determining a resonant frequency of the wireless sensor based on the comparison of the first group phase delay and second group phase delay.

16. The system of claim 15, wherein the base unit further comprises a demodulator for demodulating each of the sensor signals.

17. The system of claim 15, wherein the base unit further comprises a controller for at least one of:
controlling a switch on an antenna between transmit and receive mode;
sending the energizing signals to an RF power amplifier; and
controlling switches for receive mode.

18. The system of claim 15, wherein the signal processor uses the resonant frequency of the sensor to determine a physical parameter associated with the sensor.

19. The system of claim 18, wherein the base unit is in communication with a user interface, the signal processor being adapted to cause a numerical or graphical representation of the physical parameter to appear on the user interface.

20. The system of claim 15, wherein the signal processor determines the resonant frequency of the sensor by:
generating a first group phase delay by subtracting a first phase from a second phase;
generating a second group phase delay by subtracting the second phase from a third phase; and
comparing the first group phase delay to the second group phase delay by subtracting the first group phase delay from the second group phase delay.

21. The system of claim 15, wherein the first set of energizing signals comprise:

a first energizing signal having a frequency below an estimation of the resonant frequency;
a second energizing signal having a frequency at the estimation of the resonant frequency;
a third energizing signal having a frequency above the estimation of the resonant frequency; and
wherein the first set of sensor signals comprises:
    a first sensor signal corresponding to the first energizing signal, the first sensor signal having a first phase;
    a second sensor signal corresponding to the second energizing signal, the second sensor signal having a second phase; and
    a third sensor signal corresponding to the third energizing signal, the third sensor signal having a third phase.

22. The system of claim 21, wherein the signal processor,
identifies the resonant frequency as the second energizing frequency if the group phase delay comparison result is zero;
instructs a controller to transmit a second set of energizing signals having frequencies higher than the first set if the group phase delay comparison result is positive; and
instructs the controller to transmit the second set of energizing signals having frequencies lower than the first set if the group phase delay comparison result is negative.

23. The system of claim 15, wherein the signal processor is a digital signal processor.

\* \* \* \* \*